United States Patent
Koehler et al.

(10) Patent No.: US 12,201,465 B2
(45) Date of Patent: Jan. 21, 2025

(54) CALCULATION DEVICE FOR DETERMINING VENTILATION DEFECTS

(71) Applicant: KONINKLIJKE PHILIPS N.V., Eindhoven (NL)

(72) Inventors: Thomas Koehler, Norderstedt (DE); Jörg Sabczynski, Norderstedt (DE); Rafael Wiemker, Kisdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 838 days.

(21) Appl. No.: 17/274,798

(22) PCT Filed: Sep. 12, 2019

(86) PCT No.: PCT/EP2019/074384
§ 371 (c)(1),
(2) Date: Mar. 10, 2021

(87) PCT Pub. No.: WO2020/053345
PCT Pub. Date: Mar. 19, 2020

(65) Prior Publication Data
US 2022/0047235 A1    Feb. 17, 2022

(30) Foreign Application Priority Data
Sep. 13, 2018    (EP) .................................. 18194249

(51) Int. Cl.
*G06T 7/00*    (2017.01)
*A61B 6/00*    (2006.01)
(Continued)

(52) U.S. Cl.
CPC ............ *A61B 6/484* (2013.01); *A61B 6/4291* (2013.01); *A61B 6/50* (2013.01); *A61B 6/5217* (2013.01);
(Continued)

(58) Field of Classification Search
CPC ......... A61B 6/484; A61B 6/4291; A61B 6/50; A61B 6/5217; A61B 6/5235;
(Continued)

(56) References Cited

U.S. PATENT DOCUMENTS

| 11,058,383 | B2  |   | 7/2021  | Von Berg |          |
|------------|-----|---|---------|----------|----------|
| 2012/0300904 | A1 | * | 11/2012 | Shimada  | A61B 6/463 |
|            |     |   |         |          | 378/62   |
| 2018/0068443 | A1 | * | 3/2018  | Yin      | A61B 6/032 |

FOREIGN PATENT DOCUMENTS

| WO | WO2017055527 A1 | 4/2017 |
| WO | WO2018114553 A1 | 6/2018 |
| WO | WO2018115215 A1 | 6/2018 |

OTHER PUBLICATIONS

PCT International Search Report, International application No. PCT/EP2019/074384, Nov. 13, 2019.
(Continued)

*Primary Examiner* — Wesley J Tucker
*Assistant Examiner* — Han Hoang
(74) *Attorney, Agent, or Firm* — Larry Liberchuk

(57) ABSTRACT

The present invention relates to a calculation device (10) for comparing dark-field X-ray images. The calculation device in (10) is configured for receiving a first dark-field X-ray image (11) describing first dark-field X-ray signals of a patient at an expiration state and for receiving a second dark-field X-ray image (12) describing second dark-field X-ray signals of the patient at an inspiration state. The calculation device is further (10) configured for normalizing the first dark-field X-ray signals of the first dark-field X-ray tin image (11) with a lung thickness value describing the lung thickness at the expiration state and for normalizing the second dark-field X-ray signals of the second dark-field X-ray image (12) with a lung thickness value describing the lung thickness at the inspiration state. Further, the calcula-
(Continued)

tion device (10) is configured for comparing the normalized first dark-field X-ray signals with the normalized second dark-field X-ray signals, thereby determining a comparison result (13) and for determining whether at least one area of the patient's lung with a ventilation defect exists based on the comparison result (13).

15 Claims, 1 Drawing Sheet

(51) Int. Cl.
    *A61B 6/42*     (2024.01)
    *A61B 6/50*     (2024.01)
    *G06T 7/254*     (2017.01)
    *G16H 50/30*     (2018.01)

(52) U.S. Cl.
    CPC .......... *A61B 6/5235* (2013.01); *G06T 7/0016* (2013.01); *G06T 7/254* (2017.01); *G16H 50/30* (2018.01); *G06T 2207/10116* (2013.01); *G06T 2207/30061* (2013.01)

(58) Field of Classification Search
    CPC .................. G06T 7/0016; G06T 7/254; G06T 2207/10116; G06T 2207/30061; G16H 50/30
    See application file for complete search history.

(56) References Cited

OTHER PUBLICATIONS

Yaroshenko A. et al., "Visualization of Neonatal Lung Injury Associated with Mechanical Ventilation Using X-Ray Dark-Field Radiography", Nature, Scientific Reports, 6:24269, Oct. 20, 2015.
Gradl R. et al., "Dynamic In Vivo Chest X-Ray Dark-Field Imaging in Mice", IEEE Transactions on Medical Imaging., vol. 38, No. 2, Jul. 20, 2018, pp. 649-656, XP055557867.

* cited by examiner

CALCULATION DEVICE FOR DETERMINING VENTILATION DEFECTS

FIELD OF THE INVENTION

The present invention relates to a calculation device for comparing dark-field X-ray images, to a dark-field X-ray imaging device, to a method for determining whether at least one area of a patient's lung with a ventilation defect exists as well as to a computer program element and a computer readable medium.

BACKGROUND OF THE INVENTION

Dark-field imaging (DPCI and DFI) is a promising technology that will likely enhance the diagnostic quality of X-ray equipment Computer Tomography (CT) and radiography systems. For example, dark-field X-Ray (DAX) imaging is a new modality with a great potential in the area of diagnosing lung diseases like COPD, pulmonary fibrosis, lung cancer, etc. The basic concept for DAX imaging is to use a Talbot-Lau type interferometer, i.e., to add three gratings G0, G1, and G2 into the X-ray beam. The object can be placed either between the G0 and G1 gratings or between G1 and G2. Typically, G0 and G2 are absorber gratings and G1 is a phase grating.

A dark-field X-ray signal is generated by changes in the refractive index on a micrometre scale. For lung imaging, the dark-field X-ray signal is predominantly generated by the air-tissue interfaces in the alveoli of a patient's lung.

In certain diseases, some parts of the lung are no longer ventilated, e.g. show a ventilation defect. Clinically, it is desired to identify and to quantify the ventilation of a patient's lung, in order to monitor in a short time frame whether progression has been slowed or stopped by a particular treatment, and decide early whether therapy needs to be changed. However, there is currently no diagnostic tool which accurately determines whether a ventilation defect exists.

There is a need to address these issues.

SUMMARY OF THE INVENTION

It would be advantageous to have an improved calculation device, method and device for comparing dark-field X-ray images.

The object of the present invention is solved with the subject matter of the independent claims, wherein further embodiments are incorporated in the dependent claims. It should be noted, that the following described aspects and examples of the invention apply also to a dark-field X-ray imaging device, the method for determining whether at least one area of a patient's lung with a ventilation defect exists, as well as for the computer program element and a computer readable medium.

According to a first aspect, there is provided a calculation device for comparing dark-field X-ray images. The calculation device is configured for:

receiving a first dark-field X-ray image describing first dark-field X-ray signals of a patient at an expiration state;

receiving a second dark-field X-ray image describing second dark-field X-ray signals of the patient at an inspiration state;

normalizing the first dark-field X-ray signals of the first dark-field X-ray image with a lung thickness value describing the lung thickness at the expiration state;

normalizing the second dark-field X-ray signals of the second dark-field X-ray image with a lung thickness value describing the lung thickness at the inspiration state;

comparing the normalized first dark-field X-ray signals with the normalized second dark-field X-ray signals, thereby determining a comparison result; and determining whether at least one area of the patient's lung with a ventilation defect exists based on the comparison result.

It was found that dark-field X-ray signals from a patient's lung and normalized by the path length through the lung change with the respiratory cycle. Specifically, in expiration, the signal per length is stronger, which can be explained by the fact that the alveoli get smaller and more air-tissue interfaces are present along the X-ray. If one area with a ventilation defect exists in a patient's lung, the size change of the alveoli during the respiratory cycle will be reduced or even completely absent.

DEFINITION

In the absence of an object in the grating interferometer, the signal intensity for a detector pixel as a function of the relative grating position x follows $$I(x)=I_0(1+V\cos(\psi+2\pi x/p))$$

Where $I_0$ is the blank scan intensity, V is the blank scan visibility, and $\psi$ is the blank scan phase of the fringe pattern, and p is the period of the grating. When an object is inserted, this signal intensity is changed to $$M(x)=TI_0(1+DV\cos(\psi+\alpha+2\pi x/p))$$

Where T is the x-ray transmission, D is dark-field signal and $\psi$ is the phase shift introduced by the object.

It should be understood that throughout this disclosure the dark-field X-ray signal may be used as a synonym for the logarithm of the dark-field signal—ln D. Thus, for further processing such as normalization, the logarithmic dark-field X-ray signal as well as the dark-field X-ray signal may be used. Further, it should be noted that a dark-field X-ray system provides simultaneously a conventional X-ray transmission image and a dark-field X-ray image.

Thus, by comparing a first dark-field X-ray image at expiration with a second dark-field X-ray image at inspiration, the calculation device may be configured for determining whether at least one area of the patient's lung with a ventilation defect exists. If the patient's lung does not suffer from a ventilation defect, the normalized dark-field X-ray signals differ between expiration and inspiration. However, if one area of the patient's lung has a ventilation defect, the alveoli are not expanding/tightening as they should during the respiratory cycle, the difference in the normalized dark-field X-ray signals does not occur or occurs not as expected (difference in the dark-field X-ray signals is too low).

It should be noted, that the dark-field X-ray signals (or the logarithmic dark-field X-ray signals) are normalized by the lung thickness at expiration and the lung thickness at inspiration, respectively. Thus, the path length of the X-ray traveling through the tissue that generates the dark-field X-ray signal. The lung thickness may be determined by the calculation device by determining the in-tissue path length through the lung as described in document WO 2018/114553, which may also be performed using the transmission image which is generated by a dark-field X-ray system simultaneously to the dark-field X-ray image.

Further, the calculation device may take the logarithm of the normalized dark-field X-ray signals for further processing or calculation. These normalized dark-field X-ray signals may be compared by the calculation device thereby determining a comparison result. This comparison result may be used to determine whether one area with a ventilation defects exists or not. Therefore, the comparison result may be compared with a threshold and if the comparison result deviates from this threshold, a ventilation defect in one area of the patient's lung may be present.

Alternatively or in addition, the calculation may be configured to determine the extent of the ventilation defect in one area of the patient's lung based on the comparison result. Thus, the calculation device may quantify the ventilation defect in the patient's lung.

In other words, if the normalized first and second dark-field X-ray signals are too close to each other, the ventilation of this area of the patient's lung may be too low, and if the normalized first and second dark-field X-ray signals deviate too much from each other the ventilation of this area of the patient's lung is too high, both of which may be determined by the calculation device based on the comparison result. Further, the calculation device may determine an expected signal change between the first and second dark-field X-ray signals, which may be compared to the comparison result. The deviation between the expected signal change and the comparison result may be used to determine the extent of ventilation defect in the patient's lung.

It should be understood that the calculation device may divide the first and second dark-field images of the patient's lung into different sections, sub-section or areas, which may correlate with different section, sub-section or areas of a lung, for each of which the calculation device may determine whether a ventilation defect exists. Thus, the calculation device may compare the normalized first and second dark-field X-ray signals for each section, sub-section or area separately for determining a comparison result and for determining whether at least one area of the patient's lung with a ventilation defect exists based on the comparison result.

It should be noted that the patient's lung may be over-ventilated, ventilation is too high, or under-ventilated, ventilation is too low, both of which are encompassed by the ventilation defect.

It should be noted that the calculation device may be a processor, a calculation unit or a circuit. Further, the calculation device may comprise a memory to store data used during the calculation, e.g. the dark-field X-ray images or the output signal.

According to an embodiment, the calculation device is further configured for identifying if at least one area of the patient's lung shows a ventilation defect based on the comparison result. Thus, the calculation device may not only determine whether a ventilation effect exists or not but also identify the area with the ventilation defect of the patient's lung.

According to another embodiment, the calculation device is further configured for performing a registration of the normalized first and second dark-field X-ray images.

In other words, the calculation device may be configured to align the normalized first and second dark-field X-ray images with respect to each other, such that the same areas of the patient's lung are compared between the normalized first and second dark-field X-ray signals.

According to an embodiment, the calculation device is configured for smoothing the normalized first dark-field X-ray signals and the normalized second dark-field X-ray signals. The calculation device is preferably configured for performing the smoothing by using a low-pass filter.

In other words, the calculation device may pre-process the normalized first and second dark-field X-ray signals to reduce noise in the normalized first and second dark-field X-ray signals in order to facilitate the comparing of the normalized first and second dark-field X-ray signals. Further, the quality of the comparison result may be improved by smoothing the normalized first and second dark-field X-ray signals.

According to an embodiment, the calculation device is configured for calculating a ratio between the normalized first dark-field X-ray signals and the normalized second dark-field X-ray signals for comparing the normalized first dark-field X-ray signals with the normalized second dark-field X-ray signals. The calculation device is further configured for determining whether the at least one area of the patient's lung with the ventilation defect exists, if the calculated ratio deviates in an area by less than a first threshold from 1, wherein the first threshold is preferably 5%. However, it should be understood, that that first threshold might be 2% or 10%.

In other words, if the ratio is close to 1 or within a predefined range, e.g. between 0.95 to 1.05 (for the 5% threshold case mentioned above), the normalized first and second dark-field X-ray signals are similar. Thus, at least one area of a patient's lung with a ventilation defect exists. It should be understood, that both the ratio between the normalized first and second dark-field X-ray signals or the normalized second and first dark-field X-ray signals may be calculated and may be used for comparing the normalized first dark-field X-ray signals with the normalized second dark-field X-ray signals.

Alternatively or in addition, the calculation device may be configured to determine a value, which corresponds to the ventilation of the patient's lung based on the comparison result, such that the extent of the ventilation of that the patient's lung may be determined, e.g. 20% more or 15% less ventilated as expected.

According to an embodiment, the calculation device is configured for calculating a difference between the normalized first dark-field X-ray signals and the normalized second dark-field X-ray signals for comparing the normalized first dark-field X-ray signals with the normalized second dark-field X-ray signals. The calculation device is further configured for determining whether the at least one area of the patient's lung with the ventilation defect exists, if a mathematical norm of the calculated difference exceeds or goes below a predefined second threshold.

In other words, not only the ratio may be calculated to determine whether one area of the patient's lung with a ventilation defect exist, but also the difference, in particular, the mathematical norm of the difference, may be compared to a second threshold. If the norm of the difference is close to 0, a ventilation defect may be present in one area of the patient's lung. If the norm of the difference exceeds a certain value, the area may be over-ventilated. The second threshold may be an absolute, relative or percentage threshold.

According to another embodiment, the calculation device is configured for determining a value, which corresponds to the ventilation of the patient's lung based on the comparison result.

In other words, the calculation device may determine the ventilation state of the patient's lung or areas of the patient's lung, e.g. if an area is over- or under-ventilated. Further, the calculation device may determine the extent of these states. Further, it should be noted that the ventilation defect might be compared to the mean ventilation value, thus, an expected value for the ventilation of the patient's lung.

According to an embodiment, the calculation device is configured for determining a lung volume $V_e$ at expiration and a lung volume $V_i$ at inspiration. The lung volume may be determined by using the X-ray transmission images at expiration and inspiration, respectively. The calculation device is further configured to determine an expected mean signal change of the normalized first dark-field X-ray signals at expiration and the normalized second dark-field X-ray signals at inspiration by using the determined lung volumes $V_e$ and $V_i$. The calculation device is configured for determining whether the at least one area of the patient's lung with the ventilation defect exists based on the determined expected mean signal change and a comparison with the normalized first dark-field X-ray signals and the normalized second dark-field X-ray signals.

According to another embodiment, the expected mean signal change is derived from the equation:

$$\frac{(-\ln D_e)/l_e}{(-\ln D_i)/l_i} = \frac{V_i}{V_e} \qquad \text{Equation (1)}$$

with $(-\ln D_e)/l_e$ and $(-\ln D_i)/l_i$ as normalized dark-field X-ray signals (or the normalized logarithmic dark-field X-ray signals) for the expiration and inspiration state, $l_e$ and $l_i$ as lung thicknesses for the expiration and inspiration state, and $V_e$ and $V_i$ as lung volumes for the expiration and inspiration state.

According to an embodiment, the predefined first or second threshold is based on the ratio $V_i/V_e$ between the lung volume at inspiration $V_i$ and the lung volume at expiration $V_e$.

According to an embodiment, the calculation device is configured for generating an output signal describing the comparison result to a display unit for graphically displaying the comparison result and preferably determining whether the at least one area of the patient's lung with the ventilation defect exists.

In other words, the display unit may be configured to display the comparison result, so as to represent to comparison result to a physician. Further, the display unit may display the first and second dark-field X-ray image including the comparison result.

According to another embodiment, the output signal comprises a marked area, which corresponds to the at least one area of the patient's lung with the ventilation defect.

In other words, the at least one area with a ventilation defect of a patient's lung may be emphasized or highlighted on the display unit. The areas of the patient's lung may be colored differently or a frame may be present around the identified area of the patient's lung.

According to a second aspect, there is provided a dark-field X-ray imaging device. The dark-field X-ray imaging device comprising the before and hereinafter described calculation device. The dark-field X-ray imaging device is configured for generating the first dark-field X-ray image and the second dark-field X-ray image and for providing said images to the calculation device.

The dark-field X-ray imaging device may comprise an X-ray source, a first grating, a second grating, a third grating and an X-ray detector. The X-ray source may be configured to produce X-rays. The first grating may be positioned between the X-ray source and the second grating, wherein the second grating is positioned between the first and the third grating. A part of the region between the first grating and the third grating may form an examining region for accommodating an object, such as the patient's lung. The X-ray detector may be configured to detect at least some of the X-rays transmitted by the three gratings.

Alternatively or in addition, the dark-field X-ray imaging device may automatically acquire the first and second dark-field X-ray image at expiration and at inspiration, respectively. In another embodiment, the dark-field imaging device may be manually triggered to acquire the first and second dark-field X-ray image at expiration and at inspiration, respectively.

According to a third aspect, there is provided a method for determining whether at least one area of a patient's lung with a ventilation defect exists by using dark-field X-ray imaging data. The method comprising:

a) providing a first dark-field X-ray image describing first dark-field X-ray signals of a patient at an expiration state;

b) providing a second dark-field X-ray image describing second dark-field X-ray signals of the patient at an inspiration state;

c) normalizing, by a calculation device, the first dark-field X-ray signals of the first dark-field X-ray image with a lung thickness value describing the lung thickness at the expiration state;

d) normalizing, by the calculation device, the second dark-field X-ray signals of the second dark-field X-ray image with a lung thickness value describing the lung thickness at the inspiration state;

e) comparing, by the calculation device, the normalized first dark-field X-ray signals with the normalized second dark-field X-ray signals and determining a comparison result; and f) determining whether at least one area of the patient's lung with the ventilation defect exists based on the comparison result.

Alternatively or in addition, during the steps of normalizing the logarithm of the first and second dark-field X-ray signals may be used.

According to an embodiment, before the step of comparing the dark-field X-ray signals the following step is comprised:

smoothing the normalized first dark-field X-ray signals and the normalized second dark-field X-ray signals, wherein preferably the smoothing is performed by using a low-pass filter.

It should be noted that before the smoothing of the dark-field X-ray signals a registration of the first and second dark-field X-ray image may be performed to align the first dark-field X-ray image in relation to the second dark-field X-ray image.

According to an embodiment, the step of comparing comprises:

calculating the ratio between the normalized first dark-field X-ray signals and the normalized second dark-field X-ray signals. The at least one area of the patient's lung with the ventilation defect exists, if the calculated ratio is close to 1, e.g. it takes values in the range 1±5%.

Alternatively or in addition, the step of comparing comprises:

calculating the difference between the normalized first dark-field X-ray signals and the normalized second dark-field X-ray signals and to compare this calculated difference to a second threshold for determining whether at least one area of the patient's lung with the ventilation defect exists.

According to another aspect, there is provided a computer program element controlling device as previously described which, if the computer program element is executed by a processing unit, is adapted to perform the method steps as previously described.

According to another aspect, there is provided a computer readable medium having stored computer element as previously described.

The computer program element, can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
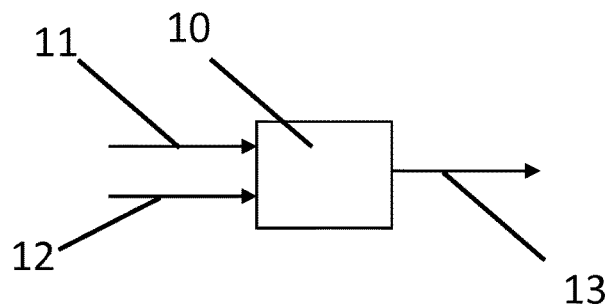
FIG. 1 shows a schematic set up of an example of a calculation device for comparing dark-field X-ray images.

FIG. 1 shows an example of a calculation device 10 for comparing dark-field X-ray images. The calculation device 10 receives a first dark-field X-ray image 11 describing first dark-field X-ray signals at expiration and receives a second dark-field X-ray image 12 describing second dark-field X-ray signals at inspiration. The calculation device 10 may normalize each one of the received dark-field X-ray signals with their corresponding lung thickness. Further, the calculation device 10 may take the logarithm of the first and second dark-field X-ray signals during normalization for further processing. After normalization, the calculation device 10 may register the first dark-field X-ray image 11 and the second dark-field X-ray image 12 to align these images in respect to each other. Furthermore, the calculation device 10 may smooth the first and second dark-field X-ray signals by a low-pass filter to reduce noise in the first and second dark-field X-ray signals for improving the result. The calculation device 10 may compare the normalized, registered and smoothened first and second dark-field X-ray signals, for example by calculating a ratio or a difference between the first and second dark-field X-ray signals. It should be noted that the ratio between the normalized first and second dark-field X-ray signals as well as the ratio between the normalized second and first dark-field X-ray signals may be calculated. The comparison leads to a comparison result 13. Based on the comparison result 13, the calculation device 10 may determine whether at least one area or section of the patient's lung with the ventilation defect exists. Therefore, the calculation device 10 may compare the comparison result 13 with a first or a second threshold to determine whether one area of the patient's lung with the ventilation defect exists. If one area of the patient's lung with ventilation defect exists, the calculation device 10 may be further configured to identify this area. In an embodiment, the comparison result 13 or the identified area of the patient's lung with the ventilation defect is displayed on a display unit. Further, the identified area of the patient's lung with the ventilation defect may be marked, emphasized or highlighted on the display unit.

In another embodiment, the calculation device 10 may be configured to determine the lung volume at expiration $V_e$ and at inspiration $V_i$ based on the additionally received first and second transmission X-ray images 11, 12. Furthermore, the calculation device 10 may be configured to determine an expected mean signal change of the normalized first and second dark-field X-ray signals at expiration and at inspiration, respectively, based on the determined lung volumes $V_e$ and $V_i$. If the comparison result deviates significantly from the determined expected mean signal change, one area of a patient's lung with a ventilation defect may be identified by the calculation device 10. The expected mean signal change may be derived from the following equation:

$$\frac{(-\ln D_e)/l_e}{(-\ln D_i)/l_i} = \frac{V_i}{V_e} \qquad \text{Equation (2)}$$

In yet another embodiment the first and second threshold may be based on the ratio of the determined lung volumes $V_i/V_e$ at expiration and at inspiration, respectively.

Figure 2:
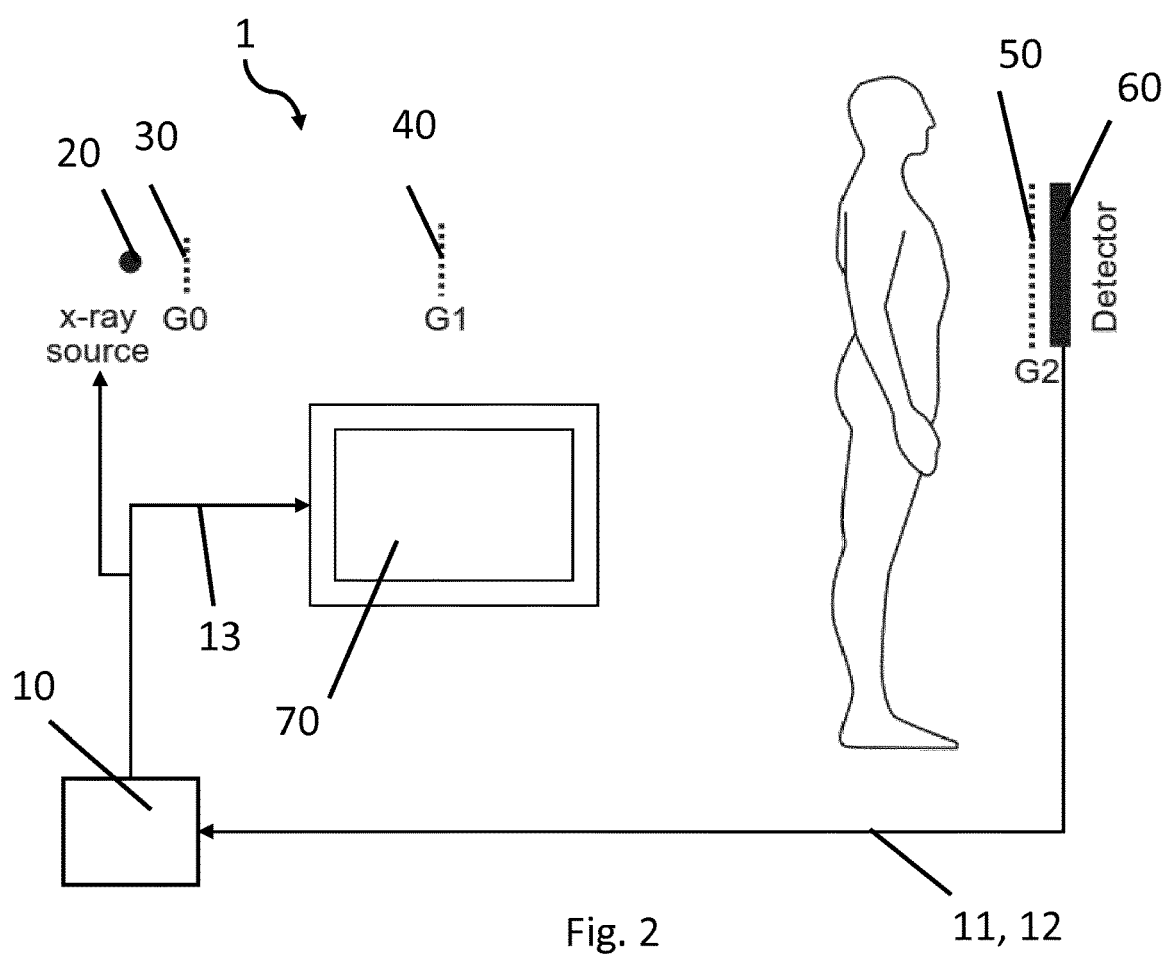
FIG. 2 shows a schematic set up of a dark-field X-ray imaging device.

FIG. 2 shows a dark-field X-ray imaging device 1 comprising the calculation device 10 according to FIG. 1. The dark-field X-ray imaging device 1 further comprises an X-ray source 20, a first grating 30, a second grating 40, a third grating 50, and an X-ray detector 60. The X-ray source 20 is configured to produce X-rays. The first grating 30 is positioned between the X-ray source 20 and the second grating 40. The second grating 40 is positioned between the first grating 30 and the third grating 50. The third grating 50 is positioned between the second grating 40 and the X-ray detector 60. At least a part of the region between the first grating 30 and the third grating 50 forms an examination region for accommodating an object, such as a patient's lung. The X-ray detector 60 is configured to detect at least some of the X-rays transmitted by the three gratings 30, 40, 50. Further, the X-ray detector 60 may be configured to detect the X-ray beam, based on which the first dark-field X-ray image 11 at expiration and the second dark-field X-ray image 12 at inspiration are generated. Further, based on the detected X-ray beam of the X-ray detected 60, the transmission images for determining the lung thickness and the lung volume may be generated. The first and second dark-field and transmission X-ray images are received by the calculation device 10, which performs the before and hereinafter described method. Further, the dark-field X-ray imaging device 1 may comprise a display unit 70, which may be configured to display the comparison result 13 of the calculation device 10. Furthermore, the calculation device 10 may trigger automatically the dark-field X-ray imaging device 1 to generate the first and second dark-field X-ray image 11, 12.

Figure 3:
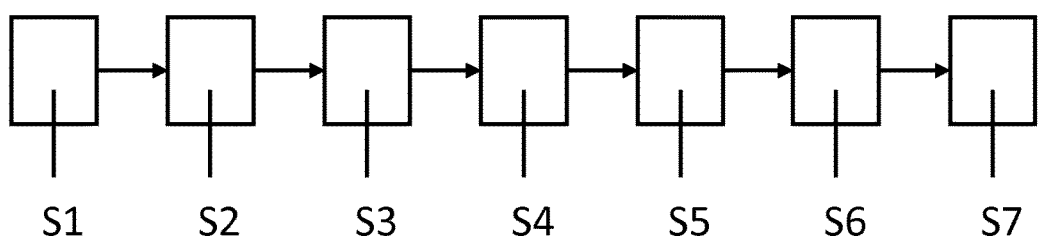
FIG. 3 shows a method for determining whether at least one area of a patient's lung with a ventilation defect exists.

FIG. 3 shows a method for determining whether at least one area of a patient's lung with a ventilation defect exists. The method comprises:

in a providing step S1, also referred to as step a), providing a first dark-field X-ray image describing first dark-field X-ray signals of a patient at an expiration state;

in a providing step S2, also referred to as step b), providing a second dark-field X-ray image describing second dark-field X-ray signals of the patient at an inspiration state;

in a normalizing step S3, also referred to as step c), normalizing, by a calculation device, the first dark-field X-ray signals of the first dark-field X-ray image with a lung thickness value describing the lung thickness at the expiration state;

in a normalizing step S4, also referred to as step d), normalizing, by a calculation device, the second dark-field X-ray signals of the second dark-field X-ray image with a lung thickness value describing the lung thickness at the inspiration state; wherein the normalizing steps S3 and S4 may taking the logarithm of the first and second dark-field X-ray signals;

in a smoothing step S5, smoothing the normalized first dark-field X-ray signals and the normalized second dark-field X-ray signals, wherein preferably the smoothing is performed by using a low-pass filter.

in a comparing step S6, also referred to as step e), comparing, by the calculation device, the normalized first dark-field X-ray signals with the normalized second dark-field X-ray signals and determining a comparison result;

wherein the comparing step S6 may comprise:

calculating the ratio between the normalized first dark-field X-ray signals and the normalized second dark-field X-ray signals, wherein the at least one area of the patient's lung with the ventilation defect exists, if the calculated ratio is close to 1, e.g. if it falls in the range 1±5%; or calculating the difference between first dark-field X-ray signals and the normalized second dark-field X-ray signals, wherein the at least one area of the patient's lung with the ventilation defect exists, if the absolute value of the calculated difference goes below a second threshold.

in a determining step S7, also referred as step f), determining whether at least one area of the patient's lung with the ventilation defect exists based on the comparison result.

In another exemplary embodiment, a computer program or computer program element is provided that is characterized by being configured to execute the method steps of the method according to one of the preceding embodiments, on an appropriate system or device.

The computer program element might therefore be stored on a computer unit, which might also be part of an embodiment. This computing unit may be configured to perform or induce performing of the steps of the method described above. Moreover, it may be configured to operate the components of the above described device and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further, on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A calculation device for comparing dark-field X-ray images, comprising:

a storage memory configured to store instructions; and
processing circuitry for executing the instructions to:
receive a first dark-field X-ray image describing first dark-field X-ray signals of a patient at an expiration state;
receive a second dark-field X-ray image describing second dark-field X-ray signals of the patient at an inspiration state;
normalize the first dark-field X-ray signals of the first dark-field X-ray image with a lung thickness value describing the lung thickness at the expiration state;
normalize the second dark-field X-ray signals of the second dark-field X-ray image with a lung thickness value describing the lung thickness at the inspiration state;
compare the normalized first dark-field X-ray signals with the normalized second dark-field X-ray signals, thereby determining a comparison result; and
determine whether at least one area of the patient's lung with a ventilation defect exists based on the comparison result.

2. The calculation device according to claim 1, further configured to identify at least one area of the patient's lung with the ventilation defect based on the comparison result.

3. The calculation device according to claim 1, further configured to perform a registration of the normalized first and second dark-field X-ray images.

4. The calculation device according to claim 1, further configured to smooth the normalized first dark-field X-ray signals and the normalized second dark-field X-ray signals.

5. The calculation device according to claim 1, further configured to calculate a ratio between the normalized first dark-field X-ray signals and the normalized second dark-field X-ray signals for comparing the normalized first dark-field X-ray signals with the normalized second dark-field X-ray signals, and to determine whether the at least one area of the patient's lung with the ventilation defect exists, if the calculated ratio is close to 1.

6. The calculation device according to claim 1, further configured to calculate a difference between the normalized first dark-field X-ray signals and the normalized second dark-field X-ray signals for comparing the normalized first dark-field X-ray signals with the normalized second dark-field X-ray signals, and to determine whether the at least one area of the patient's lung with the ventilation defect exists, if a mathematical norm of the calculated difference exceeds or goes below a predefined threshold.

7. The calculation device according to claim 6, wherein the predefined threshold is based on the ratio between the lung volume at inspiration and the lung volume at expiration.

8. The calculation device according to claim 7, wherein the output signal comprises a marked area, which corresponds to the at least one area of the patient's lung with the ventilation defect.

9. The calculation device according to claim 1, further configured to determine a value, which corresponds with the ventilation of the patient's lung based on the comparison result.

10. The calculation device according to claim 1, further configured to determine a lung volume $V_e$ at expiration and a lung volume $V_i$ at inspiration, to determine an expected mean signal change of the normalized first dark-field X-ray signals at expiration and the normalized second dark-field X-ray signals at inspiration by using the determined lung volumes $V_e$ and $V_i$, to determine whether the at least one area of the patient's lung with the ventilation defect exists based on the determined expected mean signal change and a comparison with the normalized first dark-field X-ray signals and the normalized second dark-field X-ray signals.

11. The calculation device according to claim 10, wherein the expected mean signal change is derived from:

$$\frac{(-\ln D_e)/l_e}{(-\ln D_i)/l_i} = \frac{V_i}{V_e}$$

with $D_e$ and $D_i$ as normalized dark-field X-ray signals for the expiration and inspiration state, $l_e$ and $l_i$ as lung thicknesses for the expiration and inspiration state, and $V_e$ and $V_i$ as lung volumes for the expiration and inspiration state.

12. The calculation device according to claim 1, further configured to generate an output signal describing the comparison result to a display for graphically displaying the comparison result and determining whether the at least one area of the patient's lung with the ventilation defect exists.

13. A dark-field X-ray imaging device, comprising a calculation device according to claim 1, wherein the dark-field X-ray imaging device is configured to generate the first dark-field X-ray image and the second dark-field X-ray image and provide the images to the calculation device.

14. A method for determining whether at least one area of a patient's lung with a ventilation defect exists by using dark-field X-ray imaging data, comprising:
- providing a first dark-field X-ray image describing first dark-field X-ray signals of a patient at an expiration state;
- providing a second dark-field X-ray image describing second dark-field X-ray signals of the patient at an inspiration state;
- normalizing the first dark-field X-ray signals of the first dark-field X-ray image with a lung thickness value describing the lung thickness at the expiration state;
- normalizing the second dark-field X-ray signals of the second dark-field X-ray image with a lung thickness value describing the lung thickness at the inspiration state;
- comparing the normalized first dark-field X-ray signals with the normalized second dark-field X-ray signals and determining a comparison result; and
- determining whether at least one area of the patient's lung with the ventilation defect exists based on the comparison result.

15. A non-transitory computer-readable medium for storing executable instructions, when executed by processing circuitry, cause the processing circuitry to perform a method for determining whether at least one area of a patient's lung with a ventilation defect exists by using dark-field X-ray imaging data, the method comprising:
- providing a first dark-field X-ray image describing first dark-field X-ray signals of a patient at an expiration state;
- providing a second dark-field X-ray image describing second dark-field X-ray signals of the patient at an inspiration state;
- normalizing the first dark-field X-ray signals of the first dark-field X-ray image with a lung thickness value describing the lung thickness at the expiration state;
- normalizing the second dark-field X-ray signals of the second dark-field X-ray image with a lung thickness value describing the lung thickness at the inspiration state;
- comparing the normalized first dark-field X-ray signals with the normalized second dark-field X-ray signals and determining a comparison result; and
- determining whether at least one area of the patient's lung with the ventilation defect exists based on the comparison result.

* * * * *